United States Patent [19]
Erekson et al.

[11] Patent Number: 4,956,327
[45] Date of Patent: Sep. 11, 1990

[54] MIXED BASIC METAL OXIDE/SULFIDE CATALYST

[75] Inventors: Erek J. Erekson, LaGrange; Anthony L. Lee, Glen Ellyn; S. Peter Barone, Hoffman Estates; Irvine J. Solomon, Highland Park, all of Ill.

[73] Assignee: Institute of Gas Technology, Chicago, Ill.

[21] Appl. No.: 359,500

[22] Filed: May 31, 1989

[51] Int. Cl.$^5$ .................... B01J 23/02; B01J 23/04; B01J 23/20
[52] U.S. Cl. .................... 502/216; 502/340; 585/500
[58] Field of Search ............... 502/216, 340; 585/500

[56] References Cited

U.S. PATENT DOCUMENTS

| | | | |
|---|---|---|---|
| 3,830,853 | 8/1974 | Khcheian et al. | 585/443 |
| 4,443,644 | 4/1984 | Jones et al. | 585/500 |
| 4,443,645 | 4/1984 | Jones et al. | 585/500 |
| 4,443,646 | 4/1984 | Jones et al. | 585/500 |
| 4,443,647 | 4/1984 | Jones et al. | 585/500 |
| 4,443,648 | 4/1984 | Jones et al. | 585/500 |
| 4,443,649 | 4/1984 | Jones et al. | 585/500 |
| 4,444,984 | 4/1984 | Jones et al. | 585/500 |
| 4,450,310 | 5/1984 | Fox et al. | 502/340 X |
| 4,499,322 | 2/1985 | Jones et al. | 585/500 |
| 4,499,323 | 2/1985 | Gaffney | 585/500 |
| 4,499,324 | 2/1985 | Gaffney | 585/500 |
| 4,523,049 | 6/1985 | Jones et al. | 585/500 |
| 4,774,216 | 9/1988 | Kolts et al. | 502/340 X |

OTHER PUBLICATIONS

Keller, G. E. and M. M. Bhasin, J. of Catalysis 73, 9–19, (1982).
Hinsen, W. and M. Baerns, Chem.-Ztg., 107, 223–226, (1983).
Hinsen, W., W. Bytyn and M. Baerns, Proc. 8th Int. Congr. Catal., Berlin, III 581–592, (1984).
Chemical Abstracts (USSR): 97:127153K (1982); 99:70137t (1983); 101:74734t (1984); and 101:38205n (1984).
Kirk–Othmer, Encyclopedia of Chemical Technology, Third Edition, vol. 21, Styrene, pp. 770–801.
Ward, D. J., et al., Hydrocarbon Processing, vol. 66, No. 3, Mar. 1987, pp. 47–48.
Kimble, James B. and John H. Kolts, "Oxidative Coupling of Methane to Higher Hydrocarbons," Energy Progress, vol. 6, p. 227, (1986).
Driscoll, D. J., W. M. Martir, J. Wang and J. H. Lunsford, J. Am. Chem. Soc. 107, 58–63, (1985).
Ito, T., J. Wang, C. Lin and J. H. Lunsford, J. Am. Chem. Soc. 107, 5062–64, (1985).
Illingworth, G. F. and G. W. Lester, ACS Petroleum Division Preprints, 12, No. 3, 161, (1967).
Lee, K. W., M. J. Choi, S. B. Kim and C. S. Choi, Ind. Eng. Chem. Res. 26, 1951, (1987).
Kegeyan, E. M., I. S. Vardanyan and A. B. Nalbandyan, Kinetics and Catalysis 17, No. 4, 749–754 and No. 4, 755–759, (1976).
Fiedorow, R., W. Przystajko, J. Sopa and I. G. Dalla Lana, The Nature and Catalytic Influence of Coke on Alumina: Oxidative Dehydration of Ethylbenzene, Journal of Catalysis 68, pp. 33–41, (1981).
Vrieland, G. E., Oxydehydration of Ethylbenezene to Styrene over Metal Phosphates, Journal of Catalysis 111, pp. 1–13, (1988).

Primary Examiner—W. J. Shine
Attorney, Agent, or Firm—Thomas W. Speckman; Douglas H. Pauley

[57] ABSTRACT

A mixed basic metal oxide/sulfide catalyst having the formula $$xA.yB.zC.qD$$

wherein A is an alkali metal selected from lithium, sodium, potassium, rubidium, cesium and mixtures thereof; B is a cation which has an ionization state 2 and 3 greater than the ionization state of C; B is selected from titanium, zirconium, hafnium, tantalum, niobium, vanadium and mixtures thereof; C is selected from magnesium, calcium, strontium, barium and mixtures thereof; D is selected from oxygen, sulfur and mixtures thereof; x and y are in mole fractions of z such that when $z=1$ then $x=0.001$ to 0.25, and $y=0.001$ to 0.25; and q is a number necessary to maintain charge balance with D. The sulfide form provides tolerance for sulfur containing feedstocks. The catalyst is useful for oxidative coupling of methane and aliphatic and alicyclic hydrocarbon compounds with an aromatic compound to produce higher molecular weight hydrocarbons and for dehydrogenating hydrocarbon compounds to produce unsaturated aliphatic and alicyclic chains.

21 Claims, No Drawings

MIXED BASIC METAL OXIDE/SULFIDE CATALYST

BACKGROUND OF THE INVENTION

1. Field of the Invention

This invention relates to mixed basic metal oxide/sulfide catalysts useful for production of higher hydrocarbons by oxidative coupling of methane, production of higher hydrocarbons by oxidative coupling of aliphatic and alicyclic hydrocarbon compounds with aliphatic and alicyclic substituted aromatic hydrocarbon compounds to form a longer substituent hydrocarbon on the aromatic ring, and production of unsaturated aliphatic and alicyclic chains by dehydrogenation of aliphatic and alicyclic hydrocarbon compounds and aliphatic and alicyclic substituted aromatic hydrocarbon compounds. Reaction of methane with oxygen in the presence of a mixed basic metal oxide/sulfide catalyst in accordance with this invention results in high conversion of methane with selectivity for ethane and ethylene products. Reaction of methane with toluene and oxygen in the presence of a mixed basic metal oxide/sulfide catalyst according to this invention results in high conversion to form styrene. One important dehydrogenation is the reaction of ethylbenzene in the presence of a mixed basic metal oxide/sulfide catalyst according to this invention to produce styrene.

2. Description of the Prior Art

Methane is currently available in large quantities from natural gas, anaerobic digestion of organic material, and chemical processing sources. However, use of methane as a chemical feedstock has been limited due to its high stability. It has been highly desirable to develop a catalyst for such reactions to enable operation under milder conditions with greater control over thermodynamic and kinetic processes as well as provide product selectivity and high reaction rate.

Oxidative coupling of methane to form higher hydrocarbons has been shown to be effected over a number of metal oxides, but yields of desired products have been low, as discussed by Keller, G. E. and M. M. Bhasin, J. of Catalysis 73, 9–19 (1982). Sodium and lead on alumina has been found to catalyze the formation of ethane and ethylene from methane, as disclosed in Hinsen, W. and M. Baerns, Chem.-Ztg., 107, 223–226 (1983) and Hinsen, W., W. Bytyn and M. Baerns, Proc. 8th Int. Congr. Catal., Berlin, III 581–592 (1984). Several U.S. patents teach a series of supported metal oxides which while effective for the conversion of methane to ethane and ethylene, are based on reducible metal oxides and used in a stoichiometric fashion by alternately exposing them to an oxidizing atmosphere and then to methane in the absence of oxygen. U.S. Pat. Nos. 4,443,644; 4,443,645; 4,443,646; 4,443,647; 4,443,648; 4,443,649; 4,444,984, 4,499,322; 4,499,323; 4,499,324; and 4,523,049.

Later work has demonstrated that magnesium oxide and calcium oxide, when promoted with alkali metal salts, are active for oxidative coupling of methane to ethane and ethylene in the presence of oxygen. See Kimble, James B. and John H. Kolts, "Oxidative Coupling of Methane to Higher Hydrocarbons", Energy Progress, Vol. 6, p. 227 (1986); Driscoll, D. J., W. M. Martir, J. Wang and J. H. Lunsford, J. Am. Chem. Soc. 107, 58–63 (1985); and Ito, T., J. Wang, C. Lin and J. H. Lunsford, J. Am. Chem. Soc. 107, 5062–64 (1985). These later Catalysts have the advantage of operating continuously, not requiring regeneration or pretreatment.

Borates and boron compounds have been used in partial oxidation of hydrocarbons, such as boric acid to oxidize long chain normal paraffins in the liquid phase (Illingworth, G. F. and G. W. Lester, ACS Petroleum Division Preprints, 12, No. 3, 161 (1967)) and oxidation of n-dodecane in the liquid phase to the corresponding alcohol (Lee, K. W., M. J. Choi, S. B. Kim and C. S. Choi, Ind. Eng. Chem. Res. 26, 1951 (1987)). Boric acid has been used by coating reactor walls in the combustion of methane to eliminate free radical destruction at temperatures of less than 513° C. (Kegeyan, E. M., I. S. Vardanyan and A. B. Nalbandyan, Kinetics and Catalysis 17, No. 4,749–754 and No. 4,755–759 (1976))

A number of publications describe oxidative methylation of toluene performed in Russia: Chemical Abstracts 97:127153K (I982) teaches non-catalytic methylation of toluene depended mostly on pressure and $PhMe/O/CH_4$ molar ratio; Chemical Abstracts 99:70137t (1983) teaches oxidative methylation of toluene using a Ni-V oxide or V oxide catalyst; Chemical Abstracts 101:74734t (1984) teaches oxidative methylation of toluene in presence of oxygen (max. 15 percent in reaction mixture) results in products including styrene; Chemical Abstracts 101:38205 n (1984) teaches simultaneous production of styrene, ethylbenzene, benzene, and phenols by reaction of toluene with $C_{1-4}$ alkanes in the presence of oxygen and $Fe_2O_3$ or $TiO_2$ at 600–800°. Productivity increased at higher pressure in presence of $H_2O_2$ and/or $(Me_3C)_2O_2$; and U.S. Pat. No. 3,830,853 teaches reaction of toluene with a lower paraffin hydrocarbon in the presence of oxygen at 600°–900° C. and space velocity of 2000–10000 hour$^{-1}$.

Styrene is an important commercial unsaturated aromatic monomer used extensively in the manufacture of plastics by polymerization and copolymerization. On a commercial scale, the great majority of the world's styrene is produced by dehydrogenation of ethylbenzene. A review of styrene synthesis processes is given in Kirk-Othmer, Encyclopedia of Chemical Technology, Third Edition, Vol. 21, Styrene, pgs. 770–801. One commercial process for production of styrene is the UOP Styro-Plus process using ethylbenzene and superheated steam under vacuum for the catalytic dehydrogenation of ethylbenzene as taught by Ward, D. J. et al, Hydrocarbon Processing, Vol. 66, No. 3, March 1987, pgs 47–48. Use of cokecovered alumina and boron-/alumina catalysts for oxidative dehydrogenation of ethylbenzene is taught by Fiedorow, R., W. Przystajko, M. Sopa and I. G. Dalla Lana, The Nature and Catalytic Influence of Coke on Alumina: Oxidative Dehydrogenation of Ethylbenzene, Journal of Catalysis 68, pgs. 33–41 (1981). Oxidative dehydrogenation of ethylbenzene to styrene over metal pyrophosphates, such as cerium, tin, zirconium, and titanium phosphates and calcium magnesium, strontium, barium, nickel, aluminum, thorium, zinc and silicon phosphates is taught by Vrieland, G. E., Oxydehydration of Ethylbenzene to Styrene over Metal Phosphates, Journal of Catalysis 111, pgs. 1–13 (1988). This article teaches the condensed phosphate surface is the dominant factor as a catalyst and that the cation has little or no effect.

SUMMARY OF THE INVENTION

This invention provides a mixed basic metal oxide/sulfide catalyst and catalytic process for oxidative coupling of methane to produce higher molecular weight hydrocarbons. The catalysts of this invention include a metal cation which has an ionization state 2 and 3 greater than the ionization state of a second metal cation present in the catalyst.

A mixed basic metal oxide catalyst including a metal cation which has an ionization state 1 greater than the ionization state of a second metal cation present in the catalyst and its use for oxidative coupling of methane is fully described in copending and commonly owned U.S. patent applications, Mixed Basic Oxide Catalyst for Oxidative Coupling of Methane, Ser. No. 07/172,808, filed Mar. 28, 1988, now U.S. Pat. No. 4,826,796, and Mixed Basic Metal Oxide Catalyst for Oxidative Coupling of Methane, Serial No. 07/274,415, filed Nov. 21, 1988. Oxidative coupling of aliphatic and alicyclic hydrocarbons with aliphatic and alicyclic substituted aromatic hydrocarbons using the same mixed basic metal oxide catalyst including a metal cation having an ionization state 1 greater than a second metal cation in the catalyst is fully described in copending and commonly owned U.S. patent application, Oxidative Coupling of Aliphatic and Alicyclic Hydrocarbons With Aliphatic and Alicyclic Substituted Aromati Hydrocarbons, Ser. No. 07/274,454, filed Nov. 21, 1988. Dehydrogenation of saturated hydrocarbon chains using the same mixed basic metal oxide catalyst is fully described in copending and commonly owned U.S. patent application, Dehydration of Aliphatic and Alicyclic Hydrocarbons and Aliphatic and Alicyclic Substituted Aromatic Hydrocarbons, Ser. No. 07/274,499, filed Nov. 21, 1988. A mixed basic metal sulfide catalyst in which one metal cation has an ionization state 1 greater than the ionization state of a second metal cation and its use in the above processes is described in copending and commonly owned U.S. patent application, Mixed Basic Metal Sulfide Catalyst, Ser. No. 07/359,207, filed May 31, 1989. The above copending commonly owned U.S. patent applications are fully incorporated herein by reference.

The mixed basic metal oxide/sulfide catalyst of this invention has the formula:

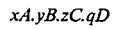

wherein A is an alkali metal selected from lithium, sodium, potassium, rubidium, cesium and mixtures thereof, preferably lithium; B is a cation which has an ionization state 2 and 3 greater than the ionization state of C; B is selected from titanium, zirconium, hafnium, tantalum, niobium, vanadium, and mixtures thereof, preferably titanium and tantalum; C is selected from magnesium, calcium, strontium, barium and mixtures thereof; preferably magnesium; D is selected from oxygen and sulfur and mixtures thereof; x and y are in the mole fractions of z such that when z=1 then x=0.001 to 0.25, preferably 0.05 to 0.15 and y=0.001 to 0.25, preferably 0.002 to 0.20; and q is a number necessary to maintain charge balance with D.

The above mixed basic metal oxide/sulfide catalyst may be used in pure oxide form or pure sulfide form and in any mixture of oxides and sulfides. The sulfide form provides sulfur tolerance to feedstocks comprising sulfur compounds, such as H$_2$S.

This invention provides a catalyst for oxidative coupling of methane to produce a higher molecular weight hydrocarbon and for oxidative coupling of aliphatic and alicyclic hydrocarbon compounds with aliphatic and alicyclic substituted aromatic hydrocarbon compounds to produce a longer substituent hydrocarbon on the aromatic ring. The reaction of an aliphatic or alicyclic hydrocarbon compound with an aliphatic or alicyclic substituted aromatic hydrocarbon compound and oxygen is conducted in the presence of a mixed basic metal sulfide catalyst at elevated temperature according to the following general reaction:

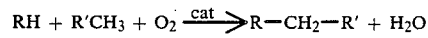

wherein R is an aliphatic or alicyclic hydrocarbon radical; and R' is an aliphatic or alicyclic hydrocarbon radical substituted on an aromatic hydrocarbon ring.

It is unexpected that catalysts active for oxidative coupling as described above involving carbon-carbon bond formation would also be active for dehydrogenation involving carbon-hydrogen bond breaking with subsequent carbon-carbon double bond formation. Dehydrogenation of saturated organics has been described by Thomas, Charles L, Catalytic Processes and Proven Catalysts, Chap. 6, Dehydrogenation, pgs. 41–45, Academic Press (1970).

This invention provides a catalyst and process for dehydrogenation of aliphatic and alicyclic chains of aliphatic and alicyclic hydrocarbon compounds and aliphatic and alicyclic substituted aromatic hydrocarbon compounds to produce an unsaturation in the hydrocarbon chain. The reaction of an aliphatic or alicyclic hydrocarbon compound, an aliphatic or alicyclic substituted aromatic hydrocarbon compound and mixtures thereof in the dehydrogenation reaction is conducted in the presence of a mixed basic metal oxide/sulfide catalyst at elevated temperature. The dehydrogenation may proceed directly according to the following general reaction of C—C bonding in a compound RH or R'CH$_3$ being converted to C=C bonding+H$_2$ or may proceed by oxidative dehydrogenation wherein C—C bonding in a compound RH or R'CH$_3$+½O$_2$ is converted to C=C bonding+H$_2$O, wherein R is an aliphatic or alicyclic hydrocarbon radical having 2 and more carbon atoms; and R' is an aliphatic or alicyclic hydrocarbon radical substituted on an aromatic hydrocarbon ring. In the case of dehydrogenation of ethylbenzene to styrene according to this invention, direct dehydrogenation proceeds according to the general reaction:

and by partial oxidation or oxidative dehydrogenation according to the general reaction:

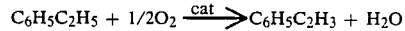

The mixed basic metal sulfide catalyst of this invention provides a catalyst which is tolerant of sulfur containing reactant compounds. Such sulfur tolerance is important when using hydrocarbon reactants derived from natural sources, such as methane obtained from gasification of coal, shale, and other natural carbonaceous materials. The maintenance of catalytic activity of the mixed basic metal sulfide catalyst of this invention in the presence of sulfur containing materials, such as H$_2$S, is of great commercial importance in view of the high cost of sulfur removal from hydrocarbons derived from naturally occurring sources.

DESCRIPTION OF PREFERRED EMBODIMENTS

The catalyst of this invention is a mixed basic metal oxide/sulfide catalyst having the formula $xA.yB.zC.qD$ wherein A, B, C, D, x, y, z and q have the meanings set forth above. In the catalyst formulation, B is a promoter on a C matrix to enhance active component A. The catalysts of this invention have metal cations with an oxidation state besides the metal, of $+4$ and $+5$ which modify a $+2$ oxidation state matrix to promote the desired product selectivity.

The mixed basic metal oxide/sulfide catalyst of this invention may be used in its pure oxide or pure sulfide form or may be used in admixture. When sulfur containing hydrocarbon feedstocks are used in the reactions catalyzed, it is preferred that the sulfide catalyst comprise over about 50 percent by weight of the total sulfide and oxide catalyst, and most preferably about 75 to about 100 percent. The mixed sulfide and oxide catalyst comprises mixed basic metal sulfide having the formula: $xA.yB.zC.qS$, wherein A is an alkali metal selected from lithium, sodium, potassium, rubidium, cesium and mixtures thereof; B is a cation which has an ionization state 2 and 3 greater than the ionization state of C; B is selected from titanium, zirconium, hafnium, tantalum, niobium, vanadium and mixtures thereof; C is selected from magnesium, calcium, strontium, barium and mixtures thereof; x and y are in mole fractions of z such that when $z=1$ then $x=0.001$ to $0.25$, and $y=0.001$ to $0.25$; and q is a number necessary to maintain charge balance with S being sulfur; in admixture with mixed basic metal oxide having the formula $x'A'.y'B'.z'C'.q'O$ wherein A' is an alkali metal selected from lithium, sodium, potassium, rubidium, cesium and mixtures thereof; B' is a cation which has an ionization state 2 and 3 greater than the ionization state of C'; B' is selected from titanium, zirconium, hafnium, tantalum, niobium, vanadium and mixtures thereof; C' is selected from magnesium, calcium, strontium, barium and mixtures thereof; x' and y' are in mole fractions of z' such that when $z'=1$ then $x'=0.001$ to $0.25$, and $y'=0.001$ to $0.25$; and q' is a number necessary to maintain charge balance with 0 being oxygen.

The mixed basic metal oxide/sulfide catalyst of this invention may be prepared by making a liquid solution of one or two soluble compounds of desired metal or metals or a colloidal suspension of solids in the liquid and adding it to a metal oxide or sulfide or mixed oxide/sulfide powder of the remaining component or components. Any liquid solutions which will retain the desired oxide or sulfide form of the metal compound are satisfactory. A wide variety of non-interfering ions may be used to form suitable liquid soluble compounds as long as they do not cause undesired chemical interference. Suitable such compounds include acids, sulfides, oxides, hydrides, nitrates, carbonates, and hydroxides. The liquid solution or colloidal suspension of one or two components is added to metal oxide/sulfide powder of the remaining component or components and well mixed followed by drying at a sufficient temperature and for a sufficient time to expel volatile components. The mixture is then crushed and sieved to a small size for catalytic use. Conventional and well known catalyst manufacturing techniques may be employed to produce the catalyst material described above. When preparing these catalytic materials, it is preferred to employ manufacturing techniques resulting in a product having a substantially uniform or homogeneous composition. Shaping of the material may be effected according to conventional techniques of the art, particularly tableting, or pelleting or extrusion. The catalyst may be used unsupported or alternatively it may be supported on an inert support as known to the art, such as alumina, silica, activated carbon and the like.

A preferred catalyst may be prepared by mixing a water soluble compound of tantalum, such as tantalum oxalate, tantalum ethoxide, or lithium tantalate and a water soluble salt of the alkali metal promoter, such as nitrate, carbonate, hydroxide, or water soluble ion with stirring to obtain complete solution of the solids. The aqueous solution of tantalum and alkali metal is added to the metal oxide powder with stirring to obtain a homogeneous mixture which may then be dried at a temperature in excess of about 110° C. The dried mixture may then be calcined at a temperature of 700° to 750° C. for a sufficient time, about 2 hours, to expel volatile portions. The mixture is then crushed and sieved to an appropriately small mesh size of about $-6$ to about $+40$, preferably about $-12$ to about $+20$ for use as a catalyst.

This invention provides gas phase oxidative coupling of methane by reaction of methane and oxygen in the presence of the above described mixed basic metal oxide/sulfide catalyst, such as a tantalum/alkali metal promoted metal oxide/sulfide catalyst. Feedstock gas comprising methane suitable for use in the process of this invention may comprise any methane containing gas which does not contain interfering compounds. Preferably, the methane containing gas used in the process of this invention comprises about 25 mole percent up to about 100 mole percent methane. Suitable sources of methane containing gas include natural gas, synthetic natural gas (SNG), product gas from gasification of carbonaceous materials, such as gasification of coal, peat, shale, and the like, as well as products of anaerobic digestion of various biomass materials. These gases principally comprise methane and may contain other hydrocarbon gases such as ethane and propane which may produce corresponding chemical reactions to those of methane in the process of this invention. Purification of such mixed gases comprising principally methane is not usually necessary, especially when using the sulfur tolerant basic metal sulfide catalyst of this invention. These sources of methane containing gas and processes for producing methane are well known in the art. The term "methane" as used throughout this disclosure and claims refers to methane as described above.

Any oxygen containing gas not containing interfering chemical compounds is useful as a feedstock in oxidative coupling according to this invention. The term "oxygen containing gas" as used throughout this disclosure and claims, refers to gas containing oxygen, such as air and gases having an oxygen content of up to 100 percent. It is preferred to use oxygen containing gas comprising over 50 volume percent oxygen. The mole percentage of oxygen relative to the mole percentage of methane in the gas mixture subjected to the process of this invention is about 2 to about 40 and preferably about 5 to about 20 mole percent oxygen.

The catalyst may be placed into a reactor, such as a tube-shell fixed bed, fluidized bed, moving bed, interbed heat exchange type, Fischer-Tropsch type, or other reactor type known to the art. Suitable reactor vessels for use at the desired operating temperatures and pressures are well known to the art. The reaction of methane and oxygen according to this invention is carried out by passing a gaseous mixture comprising methane and oxygen over the mixed basic metal oxide/sulfide catalyst as defined above at about 500° to about 1100° C., preferably about 600° to about 900° C. Suitable gas residence times are about 0.002 to about 0.00002 hour preferably about 0.0005 to about 0.0001 hour. The reaction may be carried out at about pressures of about 1 to about 1515 psia, preferably about 1 to about 150 psia.

The catalyst of this invention provides a longer hydrocarbon substituent on an aromatic ring by gas phase oxidative coupling of saturated carbon atoms of an aliphatic or alicyclic hydrocarbon compound with an aliphatic or alicyclic substituted aromatic hydrocarbon and oxygen. Suitable aliphatic and alicyclic hydrocarbon compounds for use as feedstocks in the process of this invention include straight and branched chain saturated and unsaturated aliphatic hydrocarbons, such as methane, ethane, propane, butane, heptane, pentane, hexane, octane, isobutane, isohexane, isooctane, 1-pentene, 1-hexene and mixtures thereof; cyclic chain saturated and unsaturated alicyclic hydrocarbons, such as cyclobutane, cycloheptane, cycloheptene, cyclohexane, cyclohexene and mixtures thereof; and aryl substituted aliphatic and alicyclic hydrocarbons, such as toluene, xylene, mesitylene, durene, cumene and mixtures thereof. In the case of unsaturated hydrocarbons, it should be noted that the oxidative coupling of this invention does not occur at the unsaturated bonding. Suitable aliphatic and alicyclic substituted aromatic hydrocarbon compounds for use as feedstocks in this invention are aromatic ring hydrocarbons having at least one aliphatic or alicyclic hydrocarbon radical substituent on the aromatic ring, such as toluene, xylene, indan, tetralin, and mixtures thereof.

The reactants are fed to the reaction zone in mole percent proportions of about 50 to about 90 mole percent aliphatic or alicyclic hydrocarbon compounds, preferably about 75 to about 85 mole percent; about 2 to about 40 mole percent substituted aromatic hydrocarbon, preferably about 5 to about 15 mole percent; and about 2 to about 20 mole percent oxygen, preferably about 5 to about 12 mole percent. Steam may be added in an amount of up to about 1 mole of steam per mole hydrocarbon to inhibit deep oxidation. Steam does not enter into the reaction but solely acts as an oxidation inhibitor. It is preferred to use oxygen containing gas comprising over 50 volume percent oxygen. The amounts of oxygen used in the oxidative coupling of aliphatic and alicyclic hydrocarbons with aromatic hydrocarbons are expressed as pure oxygen. The oxygen containing gas may be preheated by thermal exchange with the catalyst bed to a temperature suitable for the reaction controlling step of the process. An important aliphatic feedstock suitable for use in the process of this invention may comprise methane as described above. Important substituted aromatic feedstocks include toluene and xylene available from commercial sources.

The oxidative coupling is carried out by passing the gaseous aliphatic or alicyclic hydrocarbon and aromatic feedstocks and oxygen over the mixed basic metal oxide/sulfide catalyst as defined above at about 300° to about 1100° C., preferably about 600° to about 900° C. Suitable gas residence times are about 0.002 to about 0.00002 hour preferably about 0.0005 to about 0.0001 hour with space velocity of about 500 to about 50,000 vol/vol/hr, preferably about 1000 to about 5000 vol/vol/hr. The reaction may be carried out at about pressures of about 1 to about 1515 psia, preferably about 1 to about 150 psia, pressures above atmospheric may enhance the rate of reaction. Suitable reactor vessels for use at the above operating temperatures and pressures are well known to the art. The products of the single reactor used in the process of this invention may be passed to a simple separator for separation of the hydrocarbon product, condensate, and vent gas.

One important oxidative coupling reaction according to the process of this invention is the production of styrene directly by coupling of toluene and methane by the following reaction in the presence of the above defined catalyst:

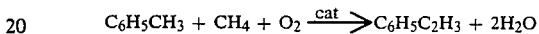

At 750° C. the heat of reaction ($\Delta H$) is $-73$ kcal/mole and the sensible heat plus the heat of vaporization of toluene is about 55 kcal/mole. Thus the process operates close to autothermal conditions after initial light-off. Conventional processes using $Fe_2O_3$ as a catalyst with $Cr_2O_3$ as a stabilizer and $K_2CO_3$ as a coke retardant for production of styrene require ethylbenzene feedstock, produced from expensive benzene and ethylene and require large amounts of superheated steam (800° C. and molar ratio 14 steam to 1 ethylbenzene) due to the conversion of ethylbenzene to styrene being endothermic. The process of this invention uses relatively inexpensive toluene, methane and air as feedstock to a single reactor where both styrene and ethylbenzene are produced in a process that does not require superheated steam.

The catalyst of this invention provides unsaturated aliphatic and alicyclic chains by dehydrogenation of saturated carbon atoms of an aliphatic or alicyclic hydrocarbon compound and an aliphatic or alicyclic substituted aromatic hydrocarbon and mixtures thereof. Suitable aliphatic and alicyclic hydrocarbon compounds for use as feedstocks in the process of this invention include straight and branched chain saturated aliphatic hydrocarbons, such as ethane, propane, butane, heptane, pentane, hexane, octane, isobutane, isohexane, isooctane and mixtures thereof; cyclic chain saturated alicyclic hydrocarbons, such as cyclobutane, cycloheptane, cyclohexane and mixtures thereof. Suitable aliphatic and alicyclic substituted aromatic hydrocarbon compounds for use as feedstocks in this invention are aromatic ring hydrocarbons having at least one saturated aliphatic or alicyclic hydrocarbon radical substituent on the aromatic ring, such as ethylbenzene, indan, tetralin and mixtures thereof.

The hydrocarbon reactant is fed to the reaction zone in contact with the above defined mixed basic metal oxide/sulfide catalyst for direct dehydrogenation and for oxidative dehydrogenation. For oxidative dehydrogenation oxygen may be added up to a mole amount of about 5 moles oxygen per mole hydro-carbon, preferably about 0.5 to about 2.0 moles oxygen per mole hydrocarbon. Steam may be added in an amount of up to about 1 mole of steam per mole hydrocarbon to inhibit undesired side reactions when oxygen is used in the feed for oxidative dehydrogenation. Steam does not enter into the reaction but solely acts as an oxidation inhibitor. For direct dehydrogenation, without oxygen in the feed, steam may be used as a heat carrying agent and up to 10 moles of steam per mole of hydrocarbon may be required.

The dehydrogenation process according to this invention is carried out by passing the gaseous aliphatic or alicyclic hydrocarbon or aromatic feedstock over the mixed basic metal oxide/sulfide catalyst as defined above at a space velocity of about 500 to about 50,000 vol/vol/hr providing gas residence times of about 0.002 to about 0.00002 hour preferably about 0.000 to about 0.00007 hour. Suitable temperatures are about 200° to about 1000° C., preferably about 600° to about 850° C. for direct dehydrogenation and preferably about 450° to about 700° C. for oxidative dehydrogenation. The reaction may be carried out at pressures of about 1 psia to about 1515 psia, preferably about 1 psia to about 25 psia for direct dehydrogenation and preferably about 1 psia to about 150 psia for oxidative dehydrogenation. Pressures above atmospheric may enhance the rate of reaction. Suitable reactor vessels for use at the above operating temperatures and pressures are well known to the art. The products of the single reactor used in the process of this invention may be passed to a simple separator for separation of the hydrocarbon product, condensate, and vent gas.

One important dehydrogenation reaction according to the process of this invention is the production of styrene directly by dehydrogenation of ethylbenzene or by oxidative dehydrogenation of ethylbenzene in the presence of the above defined mixed basic metal oxide/sulfide catalyst according to the reactions set forth above. At 727° C. the heat of reaction ($\Delta H$) for oxidative dehydrogenation is $-29.4$ kcal/mole exothermic and the sensible heat plus the heat of vaporization of ethylbenzene is about 33.0 kcal/mole. Thus the oxidative dehydrogenation process operates close to autothermal conditions after initial light-off. Conventional processes for production of styrene from ethylbenzene feedstock require large amounts of superheated steam (800° C. and molar ratio 14 steam to 1 ethylbenzene) because the conversion of ethylbenzene to styrene is endothermic. The dehydration process of this invention uses a single reactor in a process that does not require superheated steam.

The following specific examples are set forth in detail to illustrate the invention and should not be considered to limit the invention in any manner.

EXAMPLE I

A mixed basic metal oxide catalyst was prepared having the formulation 0.065 Li 0.056 Ti 1.0 Mg 1.09 O by mixing 3.00 grams $LiNO_3$, 1.15 grams concentrated $HNO_3$ and 50.52 grams of deionized water and stirred to obtain solution of the solids. The solution was slowly added over a mixture of 3.00 grams $TiO_2$ (Degussa P25) and 27.00 grams MgO powder and mixed to obtain a slurry. The slurry was dried at 110° C. overnight followed by calcining at 800° C. for one hour. The dried solids mixture was then crushed to a mesh size of $-12$ to $+20$.

Twelve grams of the above prepared catalyst was packed into a fixed bed and a gaseous feed of 60 volume percent methane and 40 volume percent air was passed through the bed at a space velocity of 4500–4600, 801° C. and 1 atmosphere pressure. Two runs were conducted with results as shown in the following Table:

TABLE I

| | Conversion of Methane % | Selectivity % Ethane + Ethylene | SCC Ethane + Ethylene/gram catalyst-hour |
|---|---|---|---|
| Run 1 | 10 | 33 | 66 |
| Run 2 | 12 | 46 | 101 |

EXAMPLE II

In a similar manner a mixed basic metal oxide of the formulation 0.058 Li 0.009 Ta 1.0 Mg 1.05 O was prepared by mixing 2.62 grams $LiNO_3$ and 1.68 grams $LiTaO_3$ with 50.06 grams deionized water and stirred until only a small amount was not dissolved. The mixture was poured over 30.00 grams MgO and stirred until a uniform slurry was obtained. The slurry was dried at 110° C. overnight, calcined at 800° C. for one hour, and the solids crushed to $-12+20$ mesh.

The prepared catalyst was loaded into a reactor and used as a methane oxidative coupling catalyst under the same conditions as in Example I resulting in 18 percent conversion of methane with 73 percent selectivity to ethane and ethylene. The rate of ethane+ethylene formation was 200 SCC/gram catalyst-hour.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A mixed basic metal oxide/sulfide catalyst having the formula:

$$xA.yB.zC.qD$$

wherein
A is an alkali metal selected from lithium, sodium, potassium, rubidium, cesium and mixtures thereof;
B is a cation which has an ionization state 2 and 3 greater than the ionization state of C;
B is selected from hafnium, tantalum, niobium, vanadium and mixtures thereof;
C is selected from magnesium, calcium, strontium, barium, and mixtures thereof;
D is selected from oxygen, sulfur and mixtures thereof;
x and y are in mole fractions of z such that when $z=1$ then $x=0.001$ to 0.25, and $y=0.001$ to 0.25; and
q is a number necessary to maintain charge balance with D.

2. A catalyst according to claim 1 wherein A is lithium, B is tantalum and C is magnesium.

3. A catalyst according to claim 1 wherein $x=0.05$ to 0.15 and $y=0.002$ to 0.20.

4. A catalyst according to claim 1 wherein A is lithium.

5. A catalyst according to claim 1 wherein C is magnesium.

6. A catalyst according to claim 1 wherein A is lithium and C is magnesium.

7. A catalyst according to claim 1 wherein D is oxygen.

8. A catalyst comprising mixed basic metal sulfide having the formula $xA.yB.zC.qS$, wherein A is an alkali metal selected from lithium, sodium, potassium, rubidium, cesium and mixtures thereof; B is a cation which has an ionization state 2 and 3 greater than the ionization state of C; B is selected from titanium, zirconium, hafnium, tantalum, niobium, vanadium and mixtures thereof; C is selected from magnesium, calcium, strontium, barium and mixtures thereof; x and y are in mole fractions of z such that when $z=1$ then $x=0.001$ to $0.25$, and $y=0.001$ to $0.25$; and q is a number necessary to maintain charge balance with S being sulfur; in admixture with mixed basic metal oxide having the formula $x'A'.y'B'.z'C'.q'O$ wherein A' is an alkali metal selected from lithium, sodium, potassium, rubidium, cesium and mixtures thereof; B' is a cation which has an ionization state 2 and 3 greater than the ionization state of C'; B' is selected from titanium, zirconium, hafnium, tantalum, niobium, vanadium and mixtures thereof; C' is selected from magnesium, calcium, strontium, barium and mixtures thereof; x' and y' are in mole fractions of z' such that when $z'=1$ then $x'=0.001$ to $0.25$, and $y'=0.001$ to $0.25$; and q' is a number necessary to maintain charge balance with 0 being oxygen.

9. A mixed sulfide and oxide catalyst according to claim 8 wherein said mixed basic metal sulfide comprises greater than about 50 weight percent of said catalyst.

10. A mixed sulfide and oxide catalyst according to claim 8 wherein said mixed basic metal sulfide comprises about 75 to 100 weight percent of said catalyst.

11. A mixed basic metal sulfide catalyst having the formula:

$$xA.yB.zC.qS$$

wherein A is an alkali metal selected from lithium, sodium, potassium, rubidium, cesium and mixtures thereof;

B is a cation which has an ionization state 2 and 3 greater than the ionization state of C;

B is selected from titanium, zirconium, hafnium, tantalum, niobium, vanadium and mixtures thereof;

C is selected from magnesium, calcium, strontium, barium, and mixtures thereof;

S is sulfur;

x and y are in mole fractions of z such that when $z=1$ then $x=0.001$ to $0.25$, and $y=0.001$ to $0.025$; and q is a number necessary to maintain charge balance with S.

12. A catalyst according to claim 11 wherein A is lithium, B is selected from the group consisting of titanium, tantalum and mixtures thereof and C is magnesium.

13. A catalyst according to claim 11 wherein $x=0.05$ to $0.15$ and $y=0.002$ to $0.20$.

14. A catalyst according to claim 11 wherein A is lithium.

15. A catalyst according to claim 11 wherein C is magnesium.

16. A catalyst according to claim 11 wherein A is lithium and C is magnesium.

17. A catalyst according to claim 8 wherein A is lithium, B is selected from the group consisting of titanium, tantalum and mixtures thereof and C is magnesium.

18. A catalyst according to claim 8 wherein $x=0.05$ to $0.15$ and $y=0.002$ to $0.20$.

19. A catalyst according to claim 8 wherein A is lithium.

20. A catalyst according to claim 8 wherein C is magnesium.

21. A catalyst according to claim 8 wherein A is lithium and C is magnesium.

* * * * *